US006742926B1

(12) United States Patent
Fesmire et al.

(10) Patent No.: US 6,742,926 B1
(45) Date of Patent: Jun. 1, 2004

(54) METHODS OF TESTING THERMAL INSULATION AND ASSOCIATED TEST APPARATUS

(75) Inventors: James E. Fesmire, Titusville, FL (US); Stanislaw D. Augustynowicz, Titusville, FL (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 0 days.

(21) Appl. No.: 09/906,018

(22) Filed: Jul. 10, 2001

Related U.S. Application Data

(60) Provisional application No. 60/217,121, filed on Jul. 10, 2000.

(51) Int. Cl.$^7$ .......................... G01N 25/00; G01N 25/20
(52) U.S. Cl. ............................. 374/45; 374/34; 374/43
(58) Field of Search ..................... 374/44, 43, 45, 374/31, 33, 34

(56) References Cited

U.S. PATENT DOCUMENTS

| 2,484,736 | A | * | 10/1949 | Razek | 374/44 |
|---|---|---|---|---|---|
| 3,242,716 | A | * | 3/1966 | Webb | 374/44 |
| 3,263,485 | A | * | 8/1966 | Mahmoodi | 374/44 |
| 3,592,060 | A | * | 7/1971 | Laverman | 374/43 |
| 3,733,887 | A | * | 5/1973 | Stanley et al. | 374/44 |
| 3,948,409 | A | | 4/1976 | Ovchinnikov et al. | |
| 4,848,103 | A | | 7/1989 | Peic et al. | |
| 4,929,089 | A | * | 5/1990 | Tsuchida | 374/44 |
| 5,537,829 | A | | 7/1996 | Jones et al. | |
| 5,589,020 | A | | 12/1996 | Varghese | |
| 5,974,784 | A | | 11/1999 | Feldman | |
| 6,331,075 | B1 | * | 12/2001 | Amer et al. | 374/44 |
| 6,487,866 | B1 | * | 12/2002 | Fesmire et al. | 62/51.1 |

FOREIGN PATENT DOCUMENTS

| DE | 3204028 A1 | * | 8/1983 | | 374/44 |
|---|---|---|---|---|---|
| JP | 55107944 A | * | 8/1980 | | 374/44 |
| JP | 03111725 A | * | 5/1991 | | 374/179 |
| JP | 04348263 A | * | 12/1992 | | 374/45 |

OTHER PUBLICATIONS

Fesmire, J., "Liquid Nitrogen Boiloff Calorimeter", NASA Research and Technology 1996 Annual Report, pp. 80–81, 1996.*
Fesmire, J., "Development Of A Multipurpose Cryostat For Insulation Testing ", NASA Research and Technology 1998 Annual Report, p. 12, 1998.*
Fesmire, J., "Insulation Testing Using A Cryostat Apparatus With Sleeve", NASA Research and Technology 1998 Annual Report, p. 10–11, 1998.*

(List continued on next page.)

*Primary Examiner*—Diego Gutierrez
*Assistant Examiner*—Mirellys Jagan
(74) *Attorney, Agent, or Firm*—Randall M. Heald; Gary G. Borda; Harry Lupuloff

(57) ABSTRACT

The system and method for testing thermal insulation uses a cryostatic insulation tester having a vacuum chamber and a cold mass including a test chamber and upper and lower guard chambers adjacent thereto. The thermal insulation is positioned within the vacuum chamber and adjacent the cold mass. Cryogenic liquid is supplied to the test chamber, upper guard and lower guard to create a first gas layer in an upper portion of the lower guard chamber and a second gas layer in an upper portion of the test chamber. Temperatures are sensed within the vacuum chamber to test the thermal insulation.

13 Claims, 8 Drawing Sheets

OTHER PUBLICATIONS

Kropschot, "Multiple Layer Insulation for Cryogenic Applications", Cryogenics, Mar. 1961, pp. 171–177.*

Kamiya et al. "Basic Design of Large Apparatus for Measuring," pp 1–4 published in 1997.

Newsletter by Cryogenic Society of America, Inc., "Cold Facts" vol. 14, #2, pp 1, 8–10, 1998.

American Society for Testing and Materials, "Standard Test Method for Heat Flux through Evacuated Insulations Using a Guarded Flat Plate Boiloff Calorimeter" pp 1–2, Sep. 1992.

NASA Lewis Research Center, "Supplemental Multilayer Insulation Research Facility," pp. 1–4, 1995, Dempsey et al.

Article of "Testing Technologies for Cryogenic Thermal Insulation Systems" published Oct. 13, 2000.

Article on "Development on Cryogenic Thermal Insulation Systems" published Oct. 13, 2000.

S. D. Augustynowicz et al., "Cryogenic Insulation Systems," pp. 1, 3, 5, & 7, 1999.

S. L. Bapat et al, "Experimental Investigations of Multilayer Insulation" pp 711–719, 1990.

J. E. Fesmire et al, "Insulation Testing Using a Cryostat Apparatus with Sleeve," pp 1–2, Jul. 1999.

Wikstrom & Fesmire, Study of Cryogenic Insulation Systems. No date.

Fesmire, "Cryostat Test Apparatus for Thermal Insulation System Development," pp 1–2, no date.

* cited by examiner

METHODS OF TESTING THERMAL INSULATION AND ASSOCIATED TEST APPARATUS

RELATED APPLICATION

This application is based upon prior filed copending provisional application Serial No. 60/217,121 filed Jul., 10, 2000.

ORIGIN OF INVENTION

The invention described herein was made in the performance of work under a NASA contract and by an employee of the United States Government and is subject to the provisions of Public Law 96-517 (35 U.S.C. §202) and may be manufactured and used by or for the Government for governmental purposes without the payment of any royalties thereon or therefore. In accordance with 35 U.S.C. §202, the contractor elected not to retain title.

FIELD OF THE INVENTION

The present invention relates to cryogenics, and more particularly, to testing of thermal insulation materials for cryogenic systems.

BACKGROUND OF THE INVENTION

Cryogenics is fundamentally about energy, and thermal insulation is about energy conservation. The technological developments of the past century have led to insulation systems that have approached the ultimate limit of performance. More technologies and markets forecast for rapid expansion into the 21st century will require, in many cases, not superinsulations but more efficient systems for a wide variety of cryogenic applications. Although bulk storage and delivery of cryogens such as liquid nitrogen, argon, oxygen, hydrogen, and helium are routinely accomplished, cryogenics is still considered a specialty. Superior methods of thermal insulation are needed.

Thermodynamics is essentially about money and is a tradeoff between refrigeration (energy bill) and the refrigerator (capital cost). In addition to the energy required to liquefy the gases, much energy is expended in the extraction or separation of these desired gases. Any product losses during storage and transfer can therefore be directly equated to monetary losses. The wide-scale proliferation of nitrogen and carbon dioxide as refrigerants is dependent on low-cost production, distribution, storage, and end-use application systems.

Cryogenic insulation is a very specialized insulation which requires very special properties. As opposed to usual insulation, cryogenic insulation must be capable of operating at very low temperatures, i.e. cryogenic temperatures between about −130° F. and −450° F., while retaining functionality, especially flexibility, at those temperatures.

Standard multi-layer insulation (MLI) systems, such as those using aluminum foil and fiberglass paper spacers, represent the benchmark for comparison. MLI or superinsulation requires a vacuum level below $10^{-4}$ torr to be effective. Other drawbacks of MLI are that it is highly anisotropic, is sensitive to compressive loads and edge effects, requires careful attention during installation, and is often limited in application by awkward structural complexities. Furthermore, the steps of evacuation, heating, and vacuum retention are costly and time consuming. Thermal performance degrades rapidly for vacuum levels above $10^{-3}$ torr.

It is important to recognize that there are three levels of thermal performance: ideal, laboratory, and industrial. Industrial (or actual) performance is typically several times worse than the laboratory performance and often 10 times worse than the ideal. The heat leak for the overall mechanical system can in turn be several times more than that estimated for the insulation system alone.

The appropriate choice of a thermal insulation system depends on matching the performance level with the overall cost. That is, the performance must justify the cost. The actual operating conditions must first be considered. An analysis of the total heat leak of the mechanical system is needed to determine the insulation requirements. Often only a common sense thermal review of the system is needed to ascertain which level of insulation material should be selected. The performance level will dictate the insulation materials and mechanical support structures or joining devices to be used.

The main factors to consider are: (1) operating conditions of the system, (2) total heat leak of the mechanical system, (3) material properties such as density and compatibility, and (4) method of testing and evaluation. Attention should also be given to offering advantages such as easier installation, maintenance, and modification where possible.

Testing of such thermal insulation materials is known. One method is the cryogenic liquid boil-off technique. The basic cryogenic liquid boil-off method is simple in concept but extremely difficult in practice. Thermal guards to reduce unwanted heat leaks to tolerable levels are required. The test articles are typically installed as blankets.

Existing boil-off apparatuses for cryogenic insulation testing are common, but few are in operation because of the extreme difficulty in obtaining accurate measurements. Many, and perhaps most, of these devices are not designed for direct thermal performance measurement and thus offer only "calculated" or "comparative" or "estimated" or "performance" k-values. Set up times are typically very lengthy. Testing of continuously rolled products (which are most commonly used) is not possible. Measurement of temperature profiles is either not done or is minimal because of the practical difficulties associated with the placement, feedthrough, and calibration of the sensors. Vacuum levels are usually restricted to one or two set points or are not actively controlled.

Thus, reliable, accurate, repeatable, and reasonable methods of testing a variety of insulation materials are desirable. The testing to obtain the necessary thermal performance and vacuum performance characteristics must be practical from the engineering point of view. A true (that is, quantitative and scientific) apparent thermal conductivity measurement (k-value) for a material system under a certain vacuum pressure level and a given pair of upper and lower boundary temperatures is needed.

More specifically, testing large size prototype material systems in a typical actual-use configuration is needed. The ability to test continuously rolled insulation materials (that is, not blanket form) is desirable because other forms such as seamed blankets will drastically affect the test results, thus giving totally inaccurate readings in most cases. The ability to quickly change out the test article with another material is also needed. Measuring the temperature profile across the thickness of the insulation is needed to characterize and understand the performance of the insulation system. Furthermore, the ability to vary the vacuum level from high vacuum to soft vacuum to atmospheric pressure is needed. This vacuum level should be maintained very steadily for long periods of time and be measured very accurately.

SUMMARY OF THE INVENTION

In view of the foregoing background, it is therefore an object of the invention to provide reliable and accurate testing of continuously rolled thermal insulation materials to measure the temperature profile across the thickness of the insulation and determine the apparent thermal conductivity thereof.

This and other objects, features and advantages in accordance with the present invention are provided by a method for testing thermal insulation in a cryostatic insulation tester comprising a vacuum chamber and a cold mass including a test chamber and upper and lower guard chambers adjacent thereto. The method includes positioning the thermal insulation within the vacuum chamber and adjacent the cold mass, supplying cryogenic liquid to the test chamber, upper guard and lower guard to create a first gas layer in an upper portion of the lower guard chamber and a second gas layer in an upper portion of the test chamber, and sensing temperatures within the vacuum chamber to test the thermal insulation.

Supplying the cryogenic liquid preferably includes continuously replenishing the cryogenic liquid to the test chamber, upper guard and lower guard until a desired vacuum level and temperatures within the vacuum chamber reach a substantially steady state, stopping the flow of the cryogenic liquid to the test chamber to create the second gas layer in the upper portion of the test chamber, and stopping the flow of the cryogenic liquid to the lower guard chamber to create the first gas layer in the upper portion of the lower guard chamber. The method may also include measuring a boil-off gas flow rate of the cryogenic liquid from the test chamber until the boil-off gas flow rate is substantially stable.

A cold boundary temperature (CBT) is defined between the insulation material and the cold mass, and a warm boundary temperature (WBT) is defined at an outer surface of the insulation material. The performance of the insulation material is preferably measured when the CBT, WBT, and temperatures of the cold mass and vacuum chamber are stable. The apparent thermal conductivity value (k) of the insulation material is measured from the measured boil-off gas flow rate, a difference between CBT and WBT, latent heat of vaporization, and the inner and outer diameters of the insulation material and effective heat transfer length of the test chamber.

The cold mass preferably includes a cylindrical cold mass, and the thermal insulation may include continuously rolled thermal insulation. Furthermore, positioning the thermal insulation within the vacuum chamber and adjacent the cold mass may include installing the continuously rolled thermal insulation around the cylindrical cold mass, enclosing the cold mass having the continuously rolled thermal insulation material installed thereon with a vacuum can and base plate, and adjusting vacuum pressure inside the vacuum chamber to a desired vacuum level.

Installing the continuously rolled thermal insulation around the cylindrical cold mass may comprise placing temperature sensors between various layers of the continuously rolled insulation material. Also, installing the continuously rolled thermal insulation around the cylindrical cold mass may include wrapping the continuously rolled thermal insulation around a cylindrical sleeve, and sliding the cylindrical sleeve over the cold mass. A gap between the sleeve and the cold mass is preferably less than 1 mm.

Furthermore, the desired vacuum level in the vacuum chamber is between $10^{-1}$ torr and 760 torr (atmospheric pressure). The temperature of the vacuum can is maintained at between approx 273 K and 373 K, and the temperature of the cold mass is maintained at approximately the normal boiling point of the cryogenic liquid (approximately 77.8 K for LN2). Cryogenic liquids may include one of liquid nitrogen, argon, oxygen, hydrogen, helium and methane.

Objects, features and advantages in accordance with the present invention are also provided by a cryostatic insulation tester including a vacuum chamber, and a cold mass within the vacuum chamber for being positioned adjacent thermal insulation being tested. The cold mass comprises a test chamber and upper and lower guard chambers adjacent thereto. A cryogenic liquid supply system is connected to the test chamber, upper guard and lower guard to create a first gas layer in an upper portion of the lower guard chamber and a second gas layer in an upper portion of the test chamber. Also, a plurality of temperature sensors are within the vacuum chamber.

The cryogenic liquid supply comprises pipes, valves and sensors to continuously replenish the cryogenic liquid to the test chamber, upper guard and lower guard until a desired vacuum level and temperatures within the vacuum chamber reach a substantially steady state, stop the flow of the cryogenic liquid to the test chamber to create the second gas layer in the upper portion of the test chamber, and stop the flow of the cryogenic liquid to the lower guard chamber to create the first gas layer in the upper portion of the lower guard chamber. A vacuum pumping system is preferably included for creating a desired vacuum level in the vacuum chamber between $10^{-7}$ torr and 760 torr. Also, a heater for maintaining a temperature of the vacuum can at between approx 273 K and 373 K may be provided.

Another aspect of the invention is a method for testing thermal insulation in a cryostat insulation tester comprising a vacuum chamber and a cold mass, including controlling a thermal coupling between the cold mass and the thermal insulation to set an elevated cold boundary temperature substantially greater than a temperature of the cryogenic liquid; and sensing temperatures within the vacuum chamber to test the thermal insulation with respect to the elevated cold boundary temperature. Positioning the thermal insulation preferably comprises installing the thermal insulation on a sleeve and sliding the sleeve over the cold mass. Controlling the thermal coupling preferably includes setting a spacing between the sleeve and cold mass. Such a gap may be between approximately 1 mm and 25 mm, for example. Controlling the thermal coupling may also include installing gap filler material (e.g. vacuum grease) between the cold mass and the sleeve, or forming the sleeve with at least one of predetermined heat transfer characteristics (thermal conductance) and a predetermined thickness. Any combination of gap spacing, sleeve material, sleeve thickness and filler material may be used to provide the desired elevated CBT.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
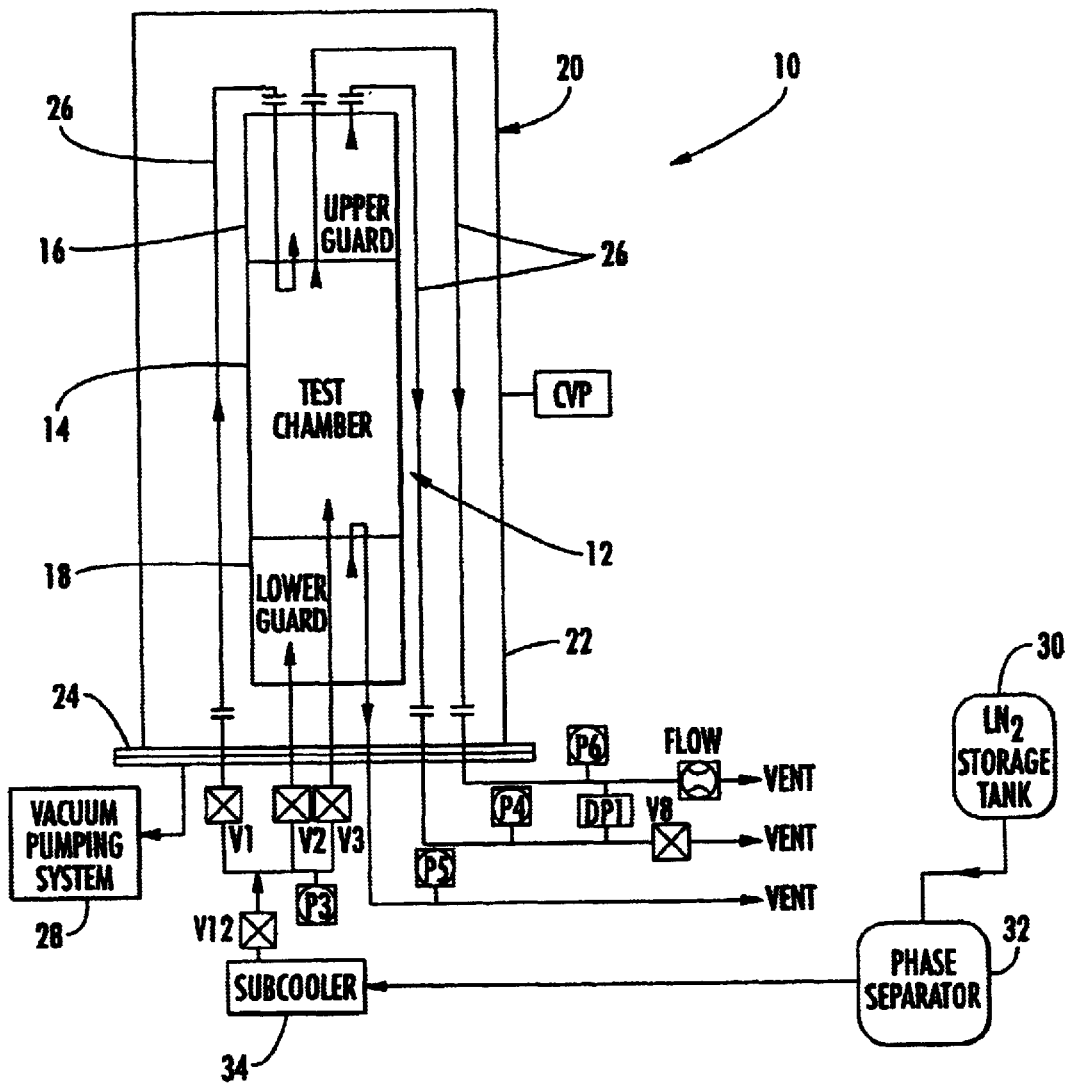
FIG. 1 is a schematic diagram of a cryostatic insulation tester according to the present invention.
Figure 2:
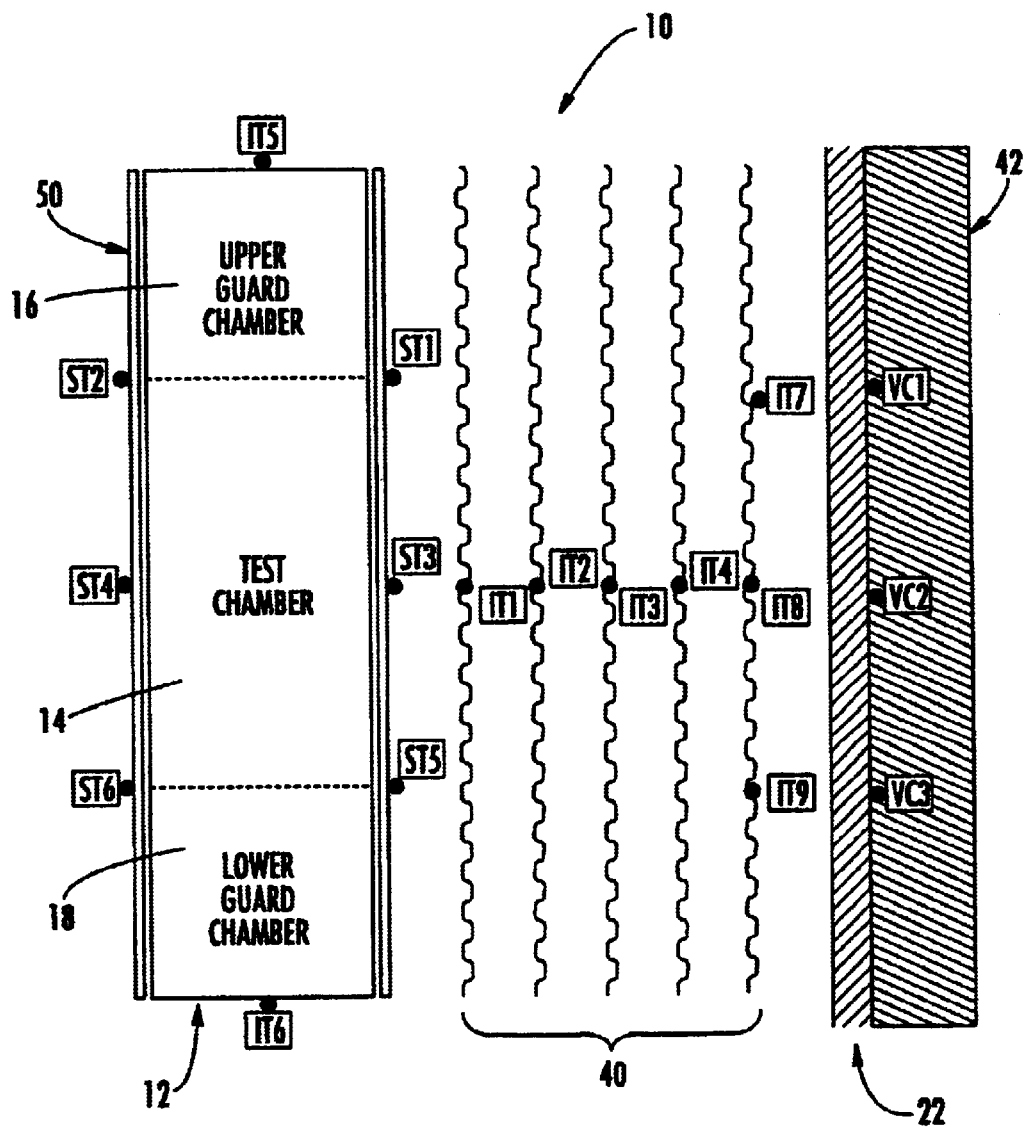
FIG. 2 is a schematic partial cross-sectional view of the cryostatic insulation tester with the layered thermal insulation and sensors installed therein.

Referring to FIGS. 1 and 2, a cryostatic insulation tester 10 according to the present invention will now be described. The cryostatic insulation tester 10 includes a cold mass 12 including a test chamber 14, upper guard 16 and lower guard 18. The cold mass 12 is enclosed in a vacuum chamber 20 created by a vacuum can 22 mounted to a base plate 24. The cryostatic insulation tester 10 is a boil-off calorimeter system (e.g. using liquid nitrogen) for direct measurement of the apparent thermal conductivity (k-value) of an insulation system at any vacuum level between $10^{-7}$ and 760 torr, for example. The cold mass is preferably a 167 mm diameter by 900 mm long cylinder constructed from heavy-wall stainless steel to provide high thermal stability and minimum axial thermal gradients. The test chamber 14 preferably has a ten liter capacity while the guard chambers 16 and 18 are preferably 2.5 liters each.

The tester 10 has a convenient top-opening configuration for easy change-out of the test article (all instrumentation and fluid feed-throughs are located on the base plate). In other words, the vacuum can 22 is removed from the base plate 24 for installation of the insulation 40 around the cold mass 12. Heavy wall stainless steel construction of the internal cold mass 12 provides maximum thermal stability and minimum temperature gradients in the axial direction. Other components of the tester 10 include pipes 26, valves V1–V3, V8 and V12, pressure sensors P3–P6 and CVP, a vacuum pumping system 28, cryogenic liquid storage tank 30, phase separator 32 and subcooler 34 as would be appreciated by the skilled artisan. The vacuum pumping system 28 includes a combination of turbo and mechanical pumps plus a finely metered gaseous nitrogen supply for controlling pumping speed.

The tester 10 is designed for testing continuously rolled insulation materials 40. Testing of blanket, loose fill, and molded product forms are also facilitated by the technology. Rolled materials 40 are preferably installed around a cylindrical sleeve 50 using a wrapping machine. The sleeve 50 is preferably copper and may be aluminum, for example. Large-size insulation test articles, e.g. 6.69-in. inside diameter by 36-in. long by up to 2-in. thick, can be fabricated and tested. The sleeve 50 is slid onto the vertical cold mass 12 of the cryostatic insulation tester 10. The gap between the cold mass and the sleeve is preferably less than 1 mm and may measure 0.035 in., for example.

Sensors IT1–IT9, ST1–ST6 and VC1–VC3 are placed throughout the tester 10 including on the outside of the sleeve 50, adjacent upper and lower ends of the cold mass 12, outside the vacuum can 22, and between layers of the insulation 40 to provide complete temperature-thickness profiles. A heater, such as a thermal shroud 42 is provided outside the vacuum can 22 to maintain a desired external temperature and heating load.

In testing, five operational sequences are performed. First, with the insulation 40 installed around the cold mass 12 and the sensors IT1–IT9, ST1–ST6 and VC1–VC3 in place, the vacuum chamber 20 is heated and pumped to obtain the desired vacuum level between $10^{-7}$ and 760 torr. Next, the chambers 14, 16 and 18 are cooled and filled with cryogenic liquid, such as liquid nitrogen LN2, at near atmospheric conditions (approximately 0.5 psig and 77.8 K). The cryostatic tester 10 is supplied with liquid nitrogen subcooled to approximately 77.8 K. The upper guard chamber 16 is kept at a slightly higher pressure (0.150±0.050 psid) than the test chamber 14 to preclude the condensation of any boil-off gas as it is exiting through the center of the guard 16.

Figure 3:
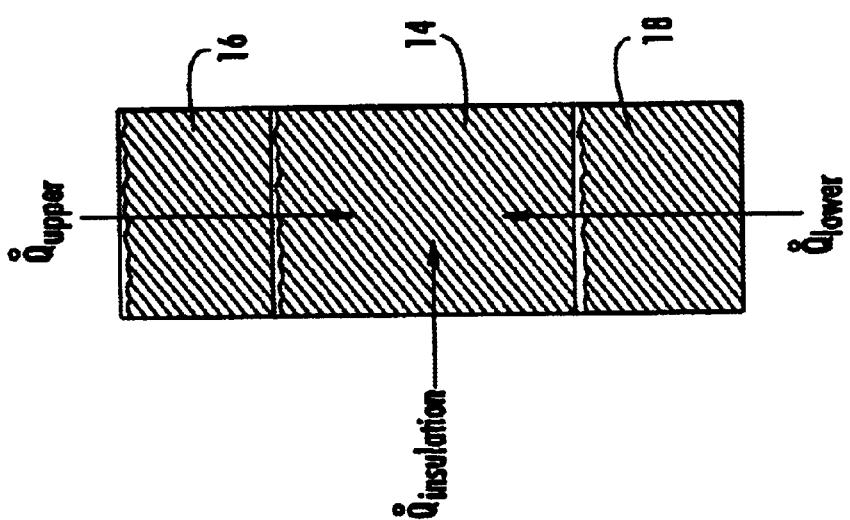

Referring to FIG. 3, a cold soak phase is illustrated where replenish/trickle flows of LN2 are maintained to all three chambers until the insulation 40 is ready for testing. For example, the cold soak can be done for as long as it takes for the insulation layer temperatures and the vacuum levels to reach stable equilibrium conditions. It is noted that the inside cold boundary temperature (CBT) is fixed at around 78 K and the outside warm boundary temperature (WBT) is fixed at between 293 K to 313 K, for example, by the thermal shroud 42. At this phase, the total heat transfer Qtotal into the test chamber 14 is the sum of the heat transfer Qins through the insulation 40, and the heat transfer Qup/Qlow through the upper and lower guards.

Figure 4:
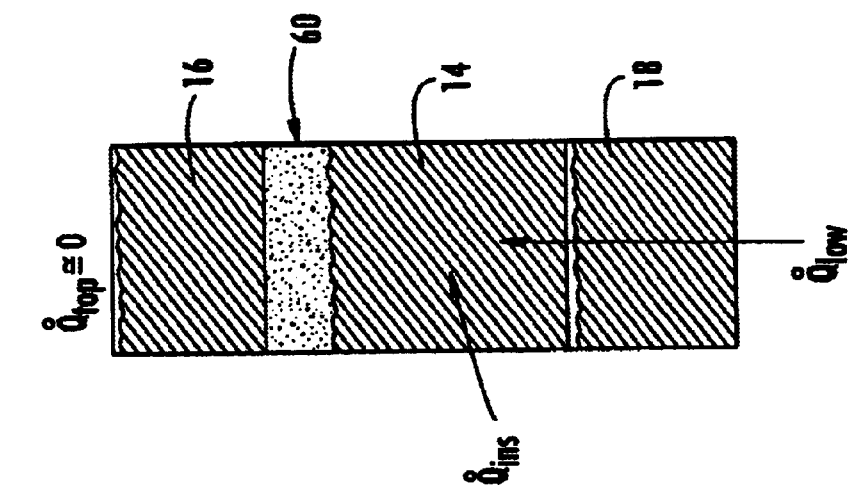

When everything is as stable as it is going to get, e.g. after about 24–36 hours, the process proceeds to a replenish boil-off phase as illustrated in FIG. 4. During this replenish boil-off phase, LN2 flow to the test chamber 14 is stopped and the boil-off gas flow rate measurement commences. The guard chambers 16, 18 are maintained at approximately 4–7 kPa for minimum heat leak and a cold gas pocket 60 is formed between the upper guard chamber 16 and the liquid surface in the test chamber 14. The heat transfer Qup from liquid to liquid at this interface is thus eliminated (any remaining heat transfer from the liquid in the upper guard chamber 16 through the cold gas pocket 60 to the liquid below in the test chamber 14 is negligible as would be appreciated by those skilled in the art). The replenish boil-off phase continues until the measured boil-off flowrate is stable.

Figure 5:
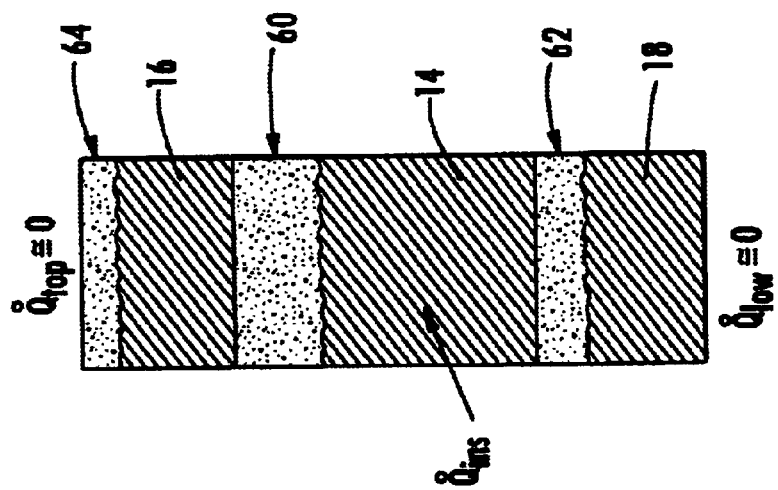
FIGS. 3–5 are schematic cross-sectional views of the cold mass illustrating the levels of cryogenic liquid during various stages of testing the thermal insulation.

The final operation is a steady state boil-off phase as illustrated in FIG. 5. LN2 flow to the guard chambers 16, 18 is stopped and cold gas pockets 62 and 64 are immediately formed. The heat transfer Qlow due to the liquid to liquid contact between the lower guard chamber 18 and the test chamber 14 is eliminated, as previously described. In conventional cryostatic testers, this lower guard liquid to test chamber liquid contact is never eliminated. Such thermal stratification in the prior art represents a serious problem because even a few tenths of a degree Kelvin in liquid to liquid temperature difference can easily be enough to overwhelm the heat transfer measurement that is desired (i.e. the heat transfer rate Qins through the insulation, normal to its surface, into the liquid in the test chamber).

The steady state measurement of insulation performance is made when all temperatures and the boil-off rate are stable. The temperatures of the cold mass 12 (e.g. maintained at 77.8 K), the sleeve 50 (CBT), the insulation 40 outer surface (WBT), and the vacuum chamber 20 (e.g. maintained at 315 K by thermal shroud) are measured. Steady-state boil-off conditions are achieved in 6 to 12 hours after an initial chilldown and thermal stabilization period of at least 24 hours, for example. All measurements are preferably recorded on a Field Point data acquisition system using LabView software.

Layer temperature profiles as a function of vacuum level indicate the three ranges (radiation, gas conduction, and convection) of dominant heat transfer modes. As discussed, heat leak through to the ends of the cryostatic tester 10 is reduced to a negligible amount by the use of the liquid nitrogen filled upper and lower guard chambers 16, 18. For this cryostatic tester 10, the measurable heat gain is from 0.2 to 20 watts (which corresponds to a boil-off flowrate of 50 to 5,000 standard cubic centimeters per minute). The surface area for a typical 1-in. thick insulation test article is 969 in$^2$. The k-value of the insulation is directly computed from the boil-off rate, latent heat of vaporization, the inner and outer diameters of the insulation material and effective heat transfer length of the test chamber, and the temperature difference WBT-CBT.

Figure 6A:
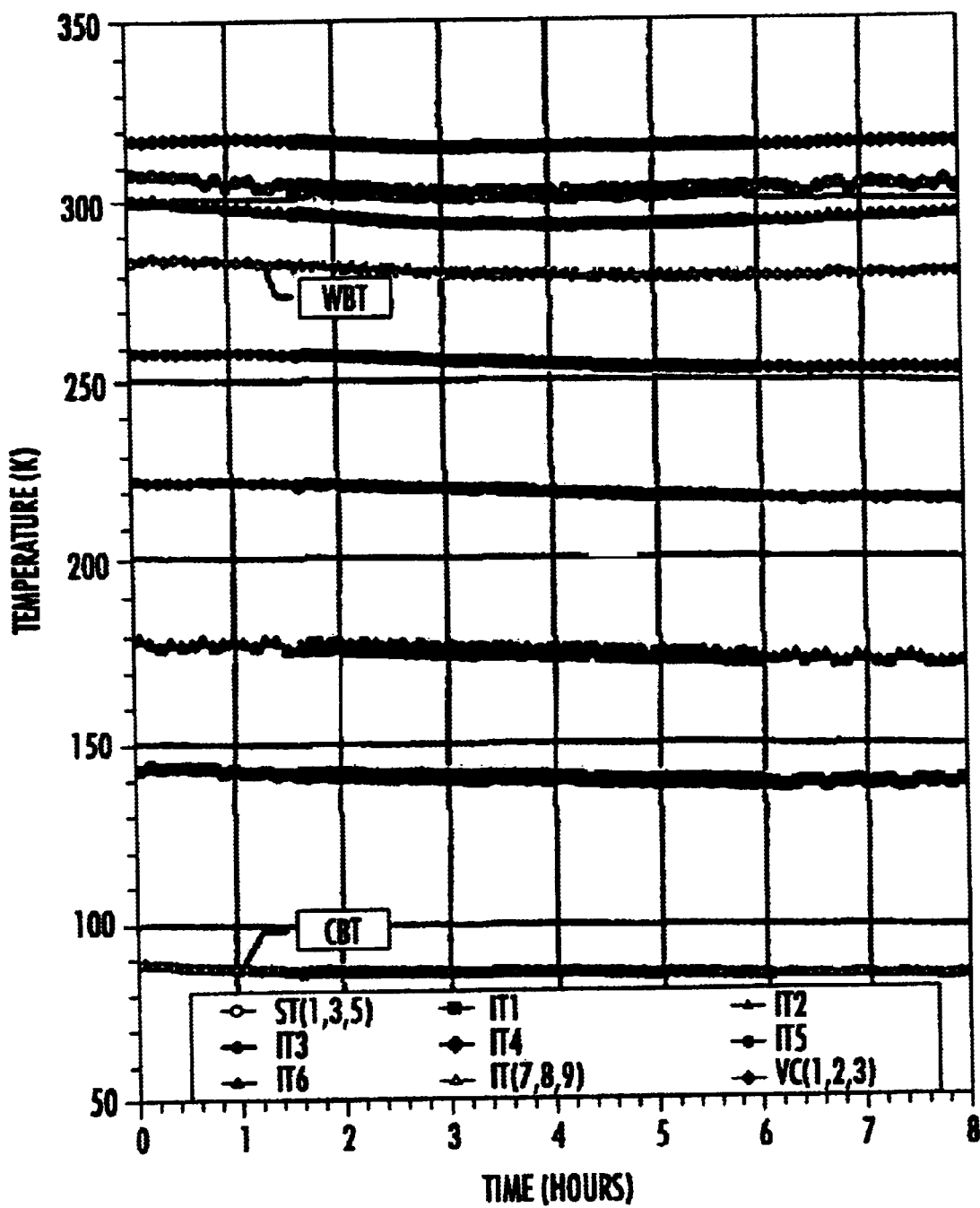
FIGS. 6(a)–6(d) are charts illustrating the parameters of an example test of the thermal insulation in the cryostatic insulation tester of FIGS. 1 and 2.
Figure 6B:
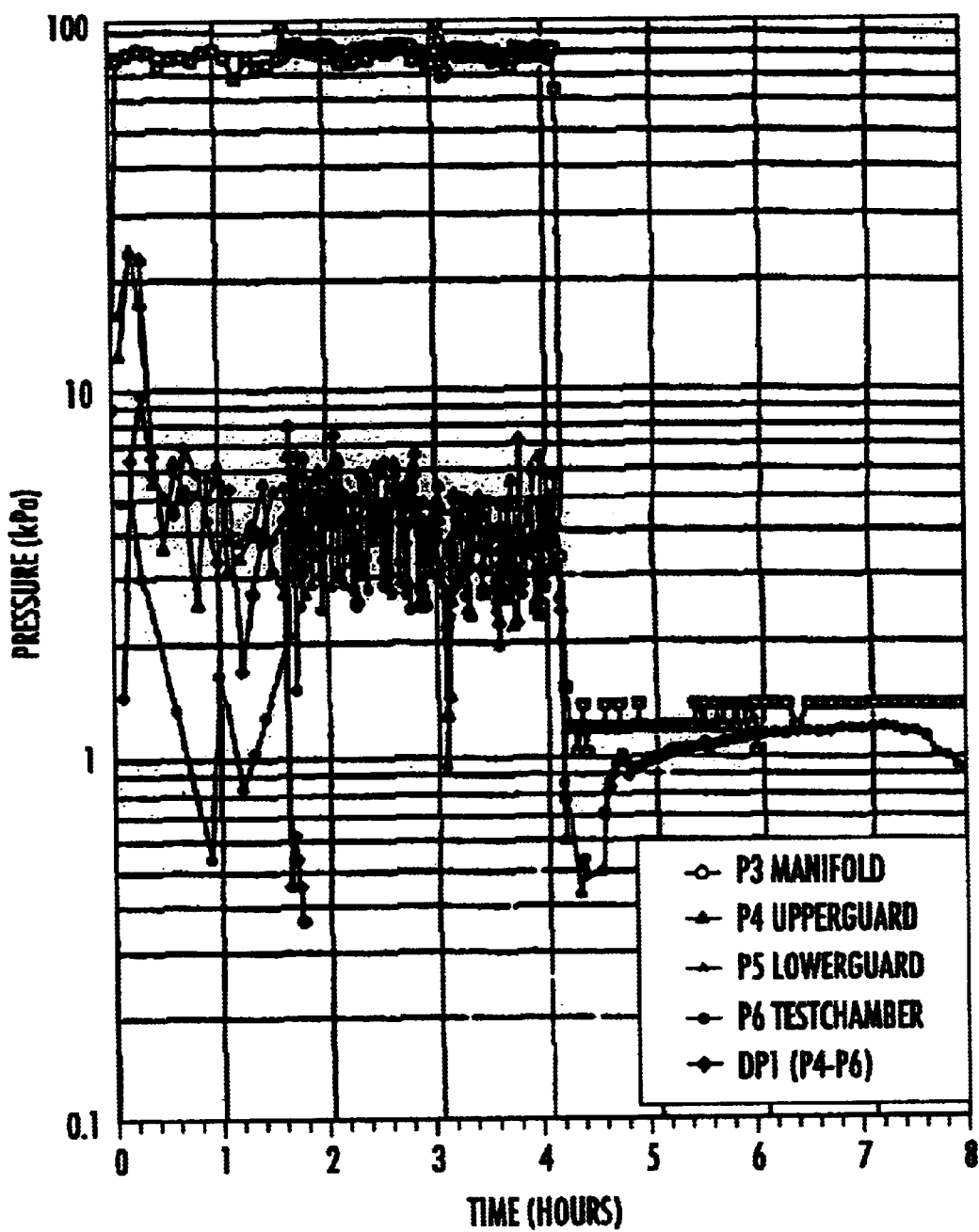
Figure 6C:
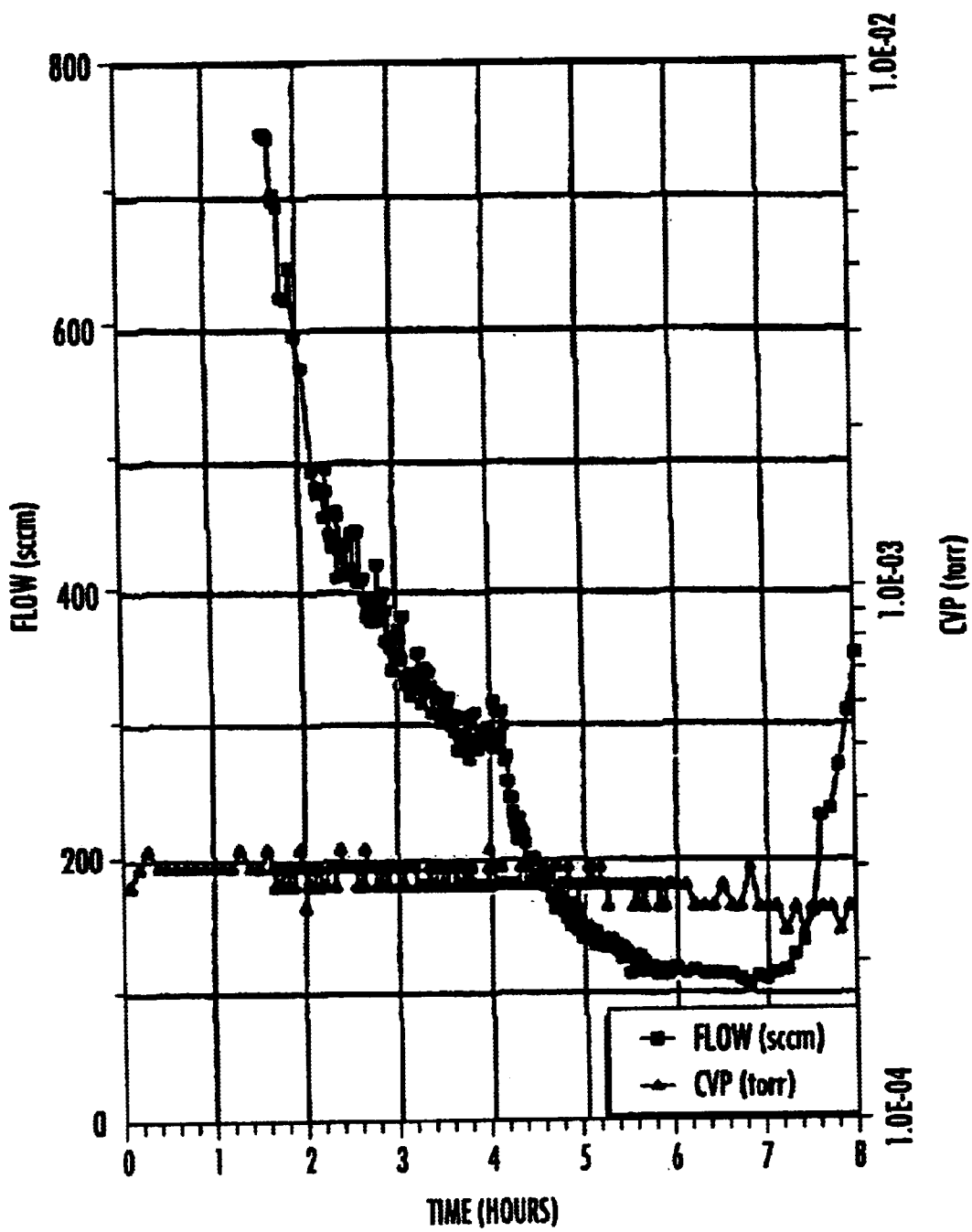
Figure 6D:
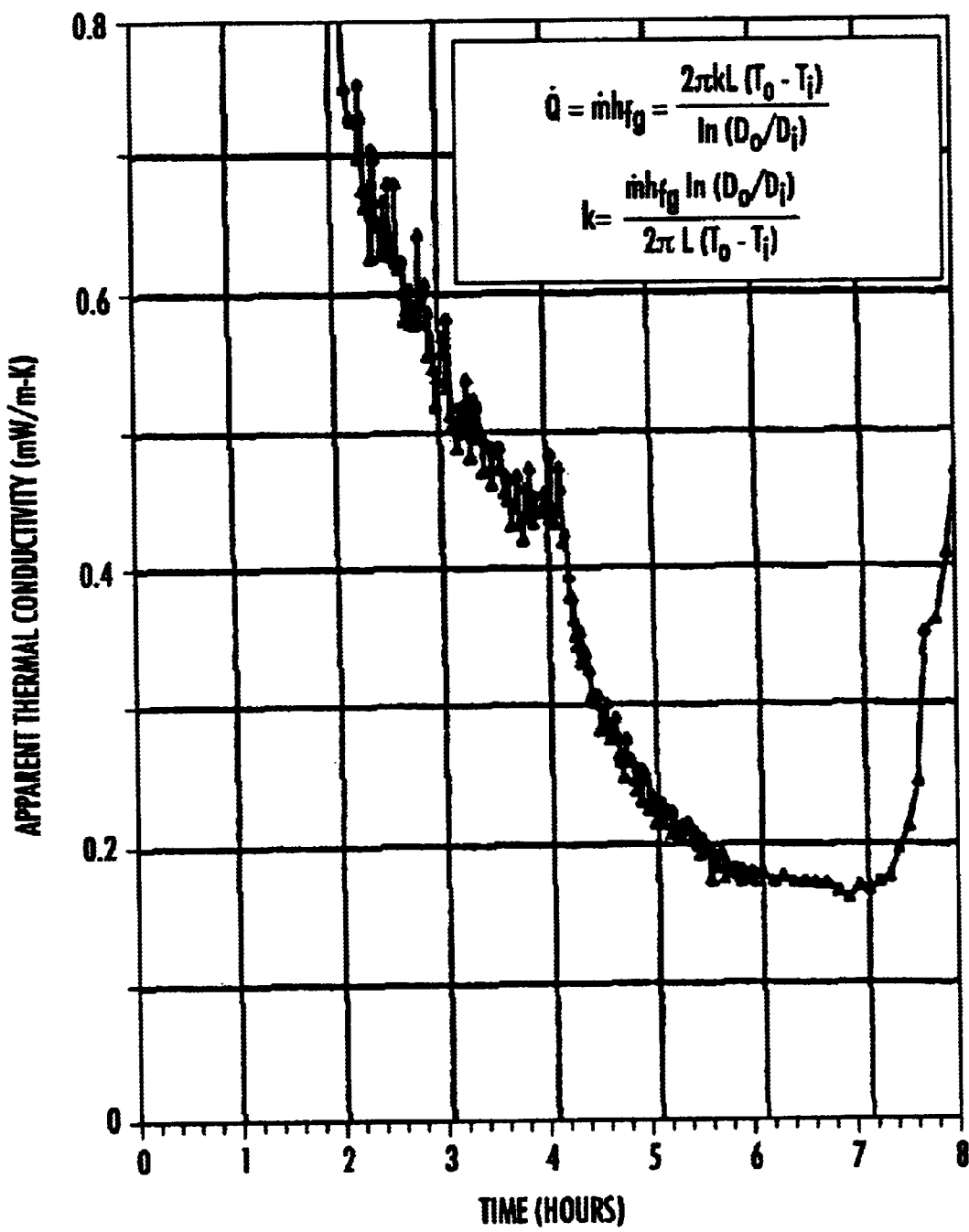

Accurate measurements require repeatable and precise operation of each element of the tester 10. Boil-off measurement in the milliwatt range require long stabilization times and carefully executed process to achieve thermal stability. This stability comes about through reaching a saturated liquid condition inside the test chamber 14 that precisely matches the guard chambers 16, 18. Test at cold vacuum pressure (CVP) above 0.1 torr are further complicated by the influence of gas conduction and convection which hinder maintaining constant boundary temperatures and a fixed vacuum level. FIGS. 6(a)–6(d) illustrate key system parameters for a typical test (including cold soak, replenish boil-off, and steady-state boil-off) of an evacuated insulation system. The layer temperature distribution is illustrated in FIG. 6(a), chamber Lns pressures are shown in FIG. 6(b), boil-off flow and CVP are charted in FIG. 6(c), and the calculated k value is illustrated in FIG. 6(d).

Figure 7:
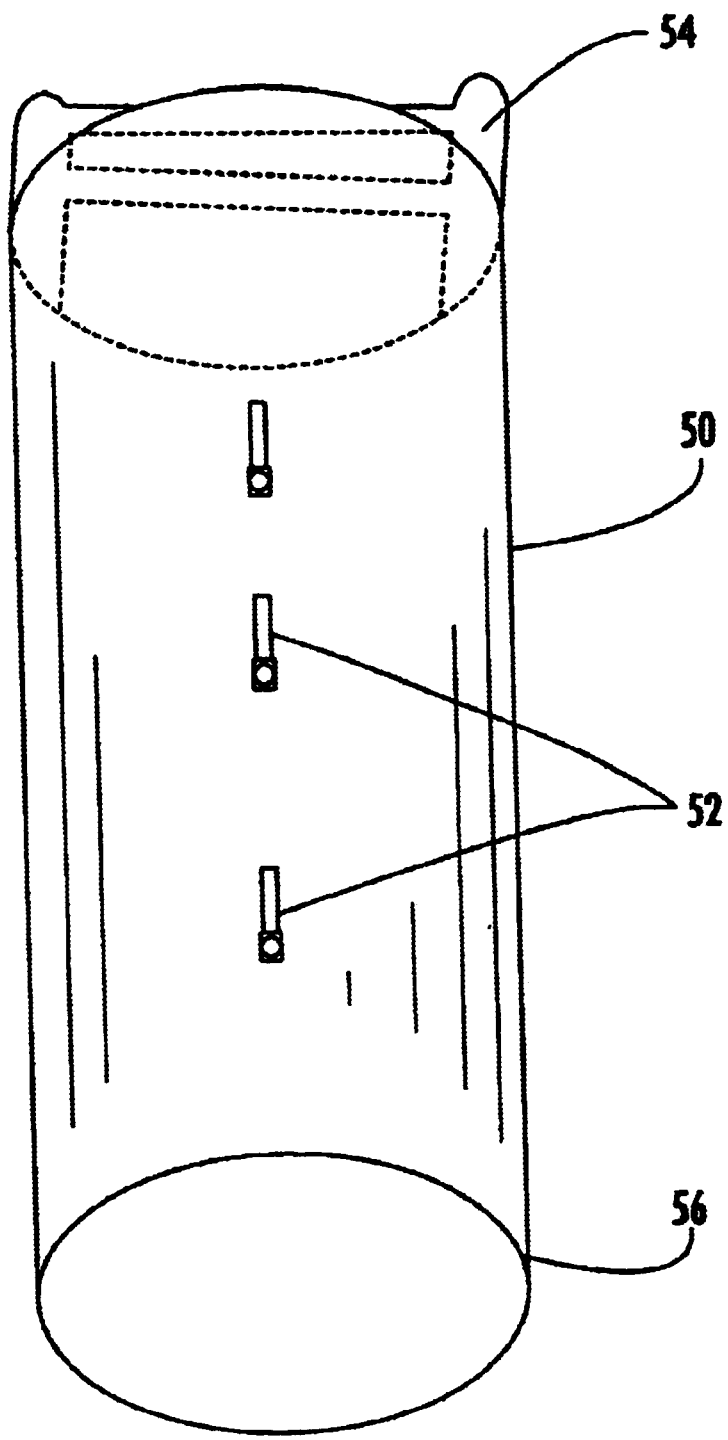
FIG. 7 is a schematic perspective view of the cylindrical sleeve of a cryostatic insulation tester according to the present invention.

Details of an example of a cylindrical sleeve 50 are described with reference to FIG. 7. As mentioned, the sleeve 50 is preferably made of copper or aluminum, for example, and can be made of any other metal or alloy which provides the appropriate level of thermal conduction. Use of the sleeve 50 provides for fabrication of insulation test articles 40 off-site and also provides support for rolled, blanket, loose-fill, poured, or molded forms. A wrapping machine is conveniently used to wrap the insulation 40 around the sleeve 50 while temperature sensors are added during the process with precision, repeatability and minimum disturbance to materials.

Additionally, the sleeve 50 may include sensor mounting blocks 52 on an outer surface thereof to facilitate the placement of the sensors ST1–ST6. The sensor mounting blocks are preferably formed of copper (e.g. $\frac{1}{16}$" h $\times \frac{1}{8}$" w $\times \frac{5}{8}$" l) and include a receiving hole with a close tolerance fit. The sensor lead wires extending from the sensor mounting blocks may be taped or glued to the surface of the sleeve 50. The sensor mounting blocks provide accurate thermal contact, convenient installation of sensors, and the ability to change out and re-use sensors.

Also, such a sleeve 50 may include a handle 54 to facilitate transport of the sleeve with the insulation installed thereon from, for example, the wrapping machine to the tester 10. Furthermore, the sleeve 50 may include a flared opening 56 to ease the installation of the sleeve over the cold mass 12 while preventing any damage from being done thereto.

The method for testing thermal insulation 40 in the cryostatic insulation tester 10 may also include controlling a thermal coupling between the cold mass 12 and the thermal insulation 40 to set an elevated cold boundary temperature substantially greater than a temperature of the cryogenic liquid LN2. The temperatures within the vacuum chamber would then be sensed to test the thermal insulation with respect to the elevated cold boundary temperature. In other words, it is possible to vary the temperature range or temperature differential for testing. Controlling the thermal coupling may include setting a spacing between the sleeve 50 and cold mass 12.

For example, increasing the gap would raise the CBT for testing. A gap between the sleeve and the cold mass may be between approximately 1 mm and 25 mm, for example. Also, controlling the thermal coupling may further include installing gap filler between the cold mass and the sleeve. Moreover, controlling the thermal coupling may comprise forming the sleeve with at least one of predetermined heat transfer characteristics and a predetermined thickness. Stable cold boundary temperature from top to bottom on the sleeve 50 may be provided by adding thermal conducting grease for high vacuum or ambient pressure tests if desired. Any combination of gap spacing, sleeve material, sleeve thickness and filler material may be used to provide the desired elevated CBT.

Methods and associated systems of the present invention for testing thermal insulation have been described to provide direct, quantitative, "scientific" measurement of (apparent) thermal conductivity k. The invention provides long duration steady state (or near steady state) measurement of heat flux through thickness of insulation test articles, full range vacuum pressure level control, set points, and accurate measurement, and complete temperature profile across thickness of insulation test article. Also, relatively quick and simple change-out of test articles is achieved with the use of the sleeve. Of course, different residual gases (atmospheres) may be used. The temperature range is from 77 K (for LN2) to about 373 K. The vacuum pressure range is from $10^{-7}$ to 760 torr. The method and system can be readily scaled up or down in size or temperature.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method for testing continuously rolled thermal insulation in a cryostatic insulation tester comprising a vacuum chamber and a cylindrically-shaped cold mass including a test chamber and upper and lower guard chambers adjacent thereto, the method comprising the steps of:
   surrounding the cylindrically-shaped cold mass with the continuously rolled thermal insulation;
   enclosing the thermal insulation and cold mass within the vacuum chamber;
   adjusting vacuum pressure inside the vacuum chamber to a desired vacuum level;
   supplying cryogenic liquid to the test chamber, upper guard and lower guard chambers to partially fill the test chamber, upper guard and lower guard chambers with liquid, creating a first gas layer in an upper portion of the lower guard chamber and a second gas layer in an upper portion of the test chamber; and
   sensing temperatures within the vacuum chamber to test the thermal insulation.

2. A method according to claim 1 wherein installing the continuously rolled thermal insulation around the cylindrically-shaped cold mass comprises the further step of placing temperature sensors between various layers of the continuously rolled insulation material.

3. A method according to claim 1 wherein the desired vacuum level is between atmospheric pressure and $10^{-7}$ torr.

4. A method according to claim 1 wherein an outer surface temperature of the insulation is maintained at between approximately 273 and 373 K, and the temperature of the cylindrically-shaped cold mass is maintained at approximately a boiling point of the cryogenic liquid.

5. A method according to claim 1 wherein the cryogenic liquid comprises one of liquid nitrogen, argon, oxygen, hydrogen, helium and methane.

6. A method according to claim 1 wherein installing the continuously rolled insulation around the cylindrically-shaped cold mass further comprises the steps of:

wrapping the continuously rolled thermal insulation around a cylindrically-shaped sleeve; and sliding the cylindrically-shaped sleeve over the cylindrically-shaped cold mass.

7. A method according to claim 6 wherein a gap between the sleeve and the cold mass is less than 1 mm.

8. A method according to claim 1 wherein supplying cryogenic liquid comprises:

continuously replenishing the cryogenic liquid to the test chamber, upper guard and lower guard chambers until a desired vacuum level and temperatures within the vacuum chamber reach a substantially steady state;

stopping the flow of the cryogenic liquid to the test chamber to create the second gas layer in the upper portion of the test chamber; and stopping the flow of the cryogenic liquid to the lower guard chamber to create the first gas layer in the upper portion of the lower guard chamber.

9. A method according to claim 8 further comprising measuring a boil-off gas flow rate of the cryogenic liquid from the test chamber until the boil-off gas flow rate is substantially stable.

10. A method according to claim 9 wherein a cold boundary temperature (CBT) is defined between the insulation material and the cold mass, and a warm boundary temperature (WBT) is defined at an outer surface of the insulation material; and further comprising measuring performance of the insulation material when the CBT, WBT, and temperatures of the cold mass and vacuum chamber are stable.

11. A method according to claim 10 further comprising the further step of determining an apparent thermal conductivity value (k) of the insulation material from the measured boil-off gas flow rate, a difference between CBT and WBT, latent heat of vaporization, and the inner and outer diameters of the insulation material and effective heat transfer length of the test chamber.

12. A method for testing thermal insulation positioned adjacent a cold mass assembly including a test chamber, an upper guard positioned adjacent one end of the test chamber and a lower guard positioned adjacent the opposite end of the test chamber comprising the following steps:

positioning the thermal insulation and the cold mass assembly within a vacuum chamber;

controlling the temperature adjacent the vacuum chamber supplying a sufficient quantity of cryogenic liquid to partially fill the test chamber and the upper and lower guards, creating a gap in the test chamber and a gap in at least the lower guard;

continuing to partially replenish the test chamber and upper and lower guards with cryogenic liquid until the temperature of the insulation material and the vacuum levels reach stable equilibrium;

stopping the flow of cryogenic liquid to the test chamber, creating a gas layer between the cryogenic liquid in the test chamber and the cryogenic liquid in the upper guard; and monitoring the boil-off gas flow rate from the test chamber until the boil-off gas flow rate is substantially stable.

13. A method according to claim 12, including the further step of stopping the flow of cryogenic liquid to both the lower and upper guards, creating a gas layer between the lower guard and the test chamber and at the end of the upper guard remote from the test chamber.

* * * * *